United States Patent [19]

Malabarba et al.

[11] Patent Number: 4,650,855
[45] Date of Patent: Mar. 17, 1987

[54] GLYCOPEPTIDE ANTIBIOTIC L 17046

[75] Inventors: Adriano Malabarba, Milan; Paolo Strazzolini, Fiume Veneto; Angelo Borghi, Milan; Bruno Cavalleri, Milan; Carolina Coronelli, Milan, all of Italy

[73] Assignee: Gruppo Lepetit S.p.A., Milan, Italy

[21] Appl. No.: 590,950

[22] Filed: Mar. 19, 1984

[30] Foreign Application Priority Data

Mar. 22, 1983 [GB] United Kingdom ................. 8307847

[51] Int. Cl.$^4$ ..................... C07C 103/52; C07H 17/08
[52] U.S. Cl. .................................. 530/322; 536/16.8; 536/18.1
[58] Field of Search ....................... 536/16.8, 18.1, 7.1; 424/180, 181; 260/112.5 R; 530/322

[56] References Cited

U.S. PATENT DOCUMENTS

| | | | |
|---|---|---|---|
| 4,239,751 | 12/1980 | Coronelli et al. | 424/118 |
| 4,357,325 | 11/1982 | Ose et al. | 514/30 |
| 4,479,897 | 10/1984 | Hunt et al. | 536/16.8 |
| 4,489,102 | 11/1984 | Waite | 424/181 |

Primary Examiner—Johnnie R. Brown
Assistant Examiner—Elli Peselev
Attorney, Agent, or Firm—Stephen L. Nesbitt

[57] ABSTRACT

The present invention is directed to a new antibiotic substance arbitrarily denominated antibiotic L 17046. This antibiotic substance is obtained from the known antibiotic substance called teicoplanin (formerly teichomycin) by chemical treatment. The new compound possesses antimicrobial activity especially against gram-positive bacteria.

2 Claims, 3 Drawing Figures

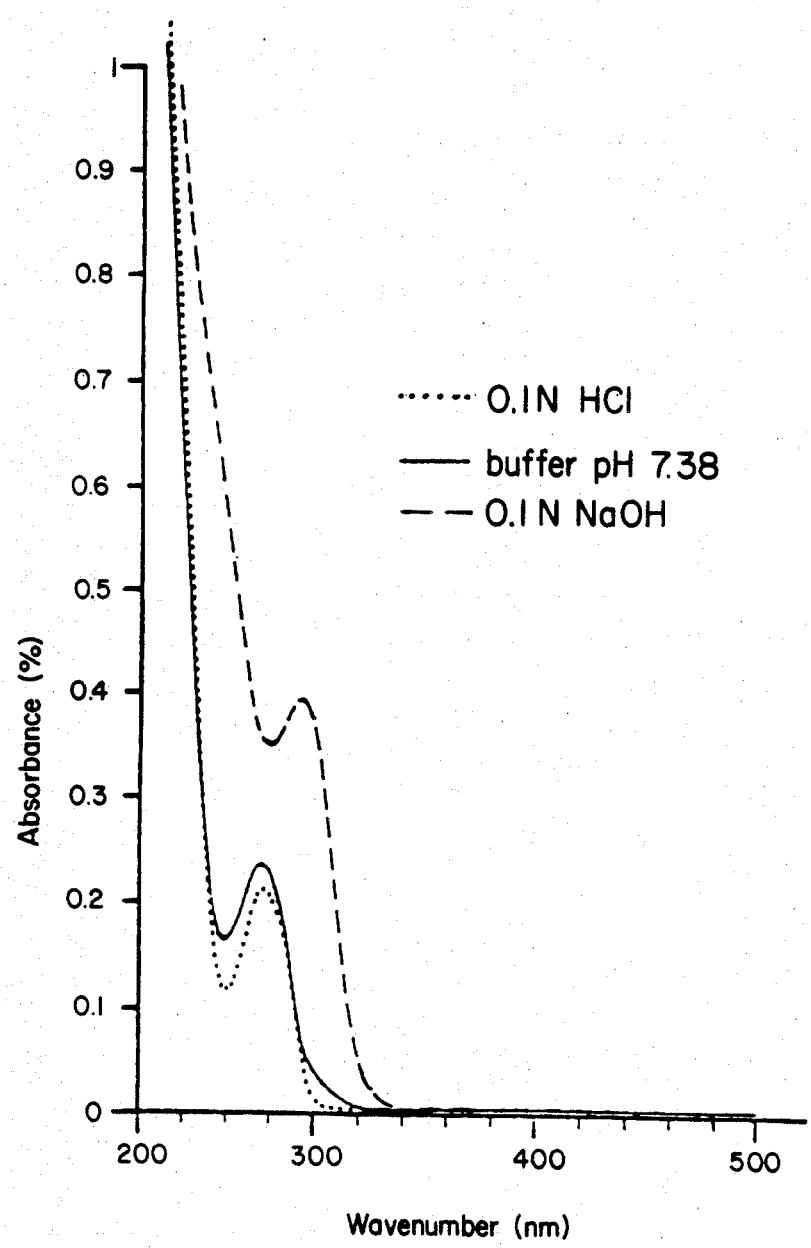
Fig. 1 UV spectrum of antibiotic L 17046

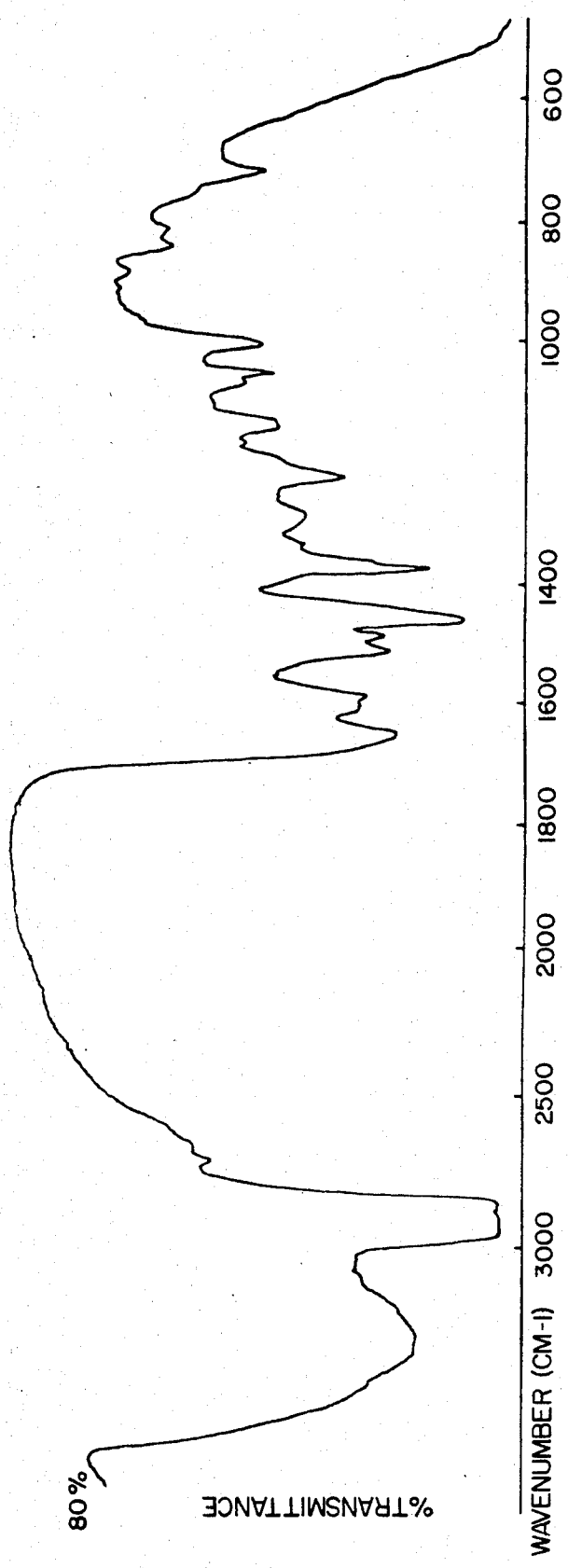
Fig. 2 IR spectrum of antibiotic L17046

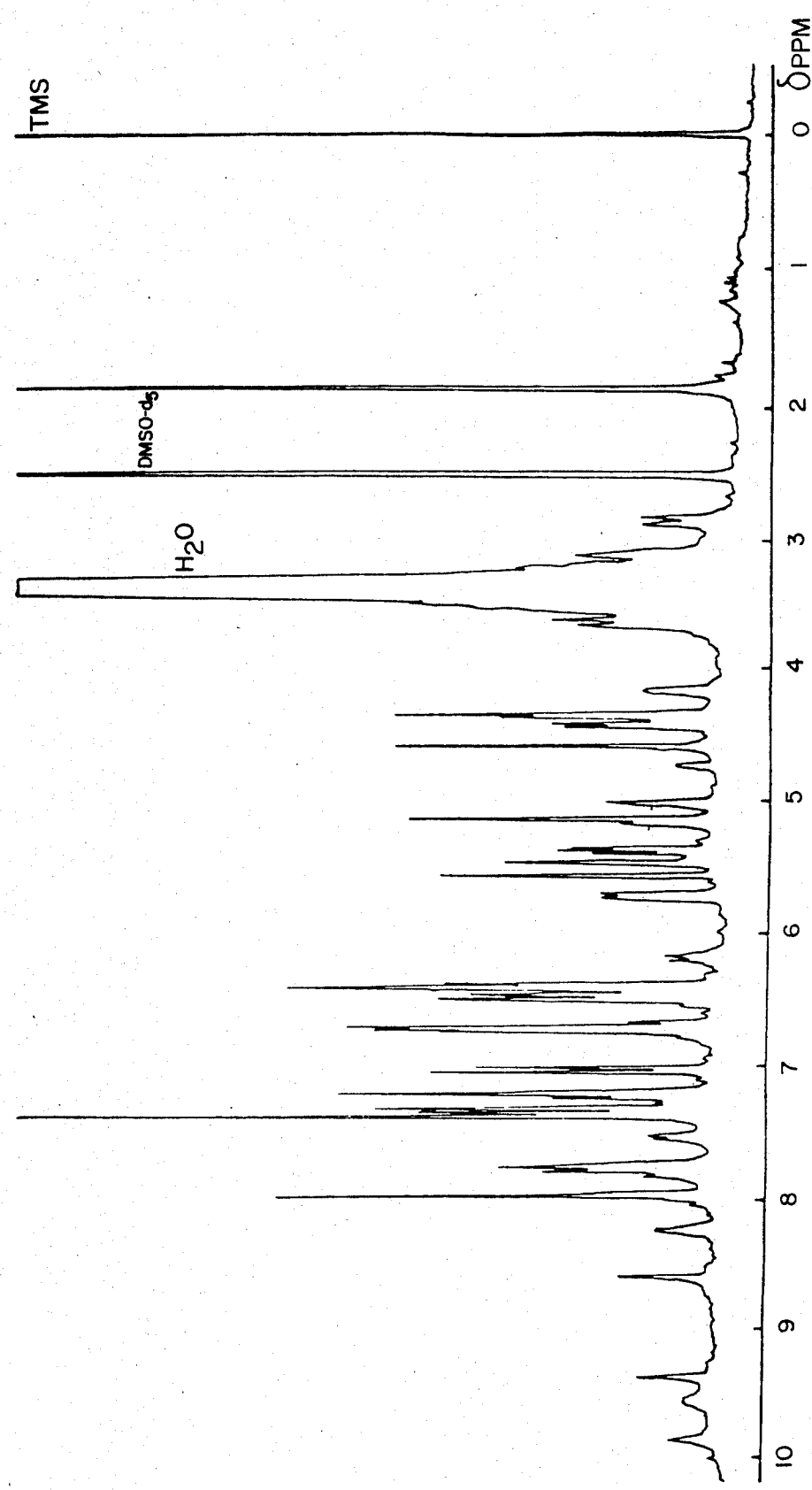
Fig. 3  $^1H$ NMR spectrum of antibiotic L17046

GLYCOPEPTIDE ANTIBIOTIC L 17046

The present invention is directed to a new antibiotic substance arbitrarily denominated antibiotic L 17046. This antibiotic substance is obtained from teicoplanin by chemical treatment.

Teicoplanin is the international non-proprietary name (INN) of the antibiotic substance formerly named teichomycin which is obtained by cultivating the strain *Actinoplanes teichomyceticus* nov. sp. ATCC 31121 in a culture medium containing assimilable sources of carbon, nitrogen and inorganic salts (see U.S. Pat. No. 4,239,.751). According to the procedure described in the above cited patent an antibiotic mixture containing teicoplanin $A_1$, $A_2$ and $A_3$ is recovered from the separated fermentation broth by extraction with a suitable water insoluble organic solvent and precipitation from the extracting solvent according to common procedures. Teicoplanin $A_2$, which is the the major factor of the isolated antibiotic complex, is then separated from the obtained antibiotic mixture by means of column chromatography on Sephadex ®.

British Patent Application Publication No. 2121401 discloses that antibiotic teicoplanin $A_2$ actually is a mixture of five closely related co-produced factors.

Surprisingly, it has now been found that it is possible to transform teicoplanin $A_2$, each of its single factors or a mixture thereof, into a different derivative which possesses antimicrobial activity. This new antibiotic substance is denominated antibiotic L 17046. The transformation is essentially a chemical transformation. In fact, under controlled acid hydrolysis conditions, teicoplanin, or the individual constituent factors thereof, gives antibiotic L 17046.

More particularly, the acid hydrolysis of teicoplanin, its single factors or a mixture thereof, in rather strong acidic conditions gives antibiotic L 17046. The concentration of the hydrolyzing agent was found to be critical. Good results can be obtained by using 1 N hydrochloric acid. However, in general, higher concentrations (up to about 3 N) can be conveniently used, depending on the reaction temperature and time. As it is apparent to the man skilled in the art, similar results can be obtained by using substantially equivalent acidic conditions, such as another mineral or organic acid of similar strength at similar concentration. The temperature can be varied depending on the strength of the mineral acid used and the reaction time. Good result are obtained by carrying out the reaction at a temperature between 70°-90° C., especially when using hydrochloric acid at a concentration between 1 N and 3 N. The reaction time, in turn, varies very much depending on the specific reaction conditions, i.e. type and concentration of the acid and reaction temperature. In general, the reaction is complete in about 40–60 minutes or more.

A co-pending application describes selective hydrolysis of teicoplanin $A_2$ or a pure factor thereof for producing an antibiotic substance denominated antibiotic L 17054. The hydrolysis is carried out under acidic conditions. The most preferred hydrolysis conditions are taught to be: the presence of about 0.5 N hydrochloric acid and a temperature of about 70°–90° C. for about 45–90 min.

This antibiotic substance (antibiotic L 17054) can in turn be transformed into the compound of the present invention by reacting it essentially under the same hydrolysis conditions as described above for the production of antibiotic L 17046 from teicoplanin $A_2$ or the pure factors threof. However, a slightly lower temperature (for example, between 50° and 70° C.), and a shorter reaction time (for example, 20 to 40 minutes) can be conveniently employed for this transformation. Although, in general, the process of the invention is preferably conducted by using a single mineral acid, it may be possible to use a mixture of different acids in order to obtain reaction conditions similar to those outlined above when dealing with a single hydrolyzing agent. In general, the possibility of these substitutions and the suitable mixtures of hydrolytic agents are apparent to the skilled man who is also able to select the proper reaction temperature and time on the basis of what is disclosed in the present application and what is generally known in the art. Each reaction step is monitored, as known in the art, by means of TLC or preferably HPLC technics. Also chromatographic techniques coupled with bioassay tests (e.g. autobioassay) using microorganisms susceptible to the antibiotic substance L 17046 can be conveniently used.

The compound which forms, antibiotic L 17046, is in general insoluble in highly concentrated mineral acids and precipitates. Precipitation may be aided as known in the art, for instance, by addition of non-solvents. The recovered crude product is then purified preferably by means of chromatographic techniques. In particular, partition column chromatography is preferred. A preferred absorbent is in this case uniform particle-size silica gel.

The eluent is preferably a mixture of acetonitrile and water, but eluent mixtures of solvents having a similar polarity can be conveniently used.

The preferred eluent mixture is represented by a linear gradient mixture of acetonitrile and water from about 83:17 to about 70:30. The flow rate is preferably about 357 ml/h.

The elution is monitored by chromatographic assays, preferably HPLC.

The collected fractions are pooled according to the antibiotic content. Pure antibiotic L 17046 is then recovered by following known per se techniques, such as precipitation by non-solvents, filtration or extraction with solvents, concentration to a small volume and precipitation.

Antibiotic L 17046 has the following characteristics:

(a) the specific rotation $[\alpha]_D^{20}$ is $-44°$ (c=1%, DMF)

(b) it is freely soluble in water at pH>8.0, in dimethylformamide, dimethylsulfoxide, propyleneglycol and methylcellosolve; sligltly soluble in methanol; almost insoluble in n-hexane, ethyl ether and acetone.

(c) it has an ultraviolet absorption spectrum, which is given in FIG. 1 of the accompnaying drawings, that exhibits the following absorption maxima:

in 0.1 N hydrochloric acid: $\lambda_{max}278$ nm ($E_1$ $cm^{1\%}=67.1$)

in 0.1 N sodium hydroxide: $\lambda_{max}297$ nm ($E_1$ $cm^{1\%}=124.1$)

in phosphate buffer pH 7.4: $\lambda_{max}277$ nm ($E_1$ $cm^{1\%}=75.0$)

(d) an infrared absorption spectrum in nujol, shown in FIG. 2 of the accompanying drawings, with the following observable absorption maxima ($cm^{-1}$): 3700–2000, 2970–2850 (nujol), 1655, 1610, 1595, 1515, 1490, 1460 (nujol), 1375 (nujol), 1300, 1230, 1145, 1060, 1010, 890, 850, 820, 720 (nujol)

(e) an elemental analysis, after the sample has been previously dried at about 140° C. under inert atmosphere (weight loss=8.4%), which indicates the following approximate percentage composition (average): carbon 56.74%; hydrogen, 4.27%; nitrogen, 7.99%; chlorine, 5.11%; ashes, 0.6%

(f) the following $R_f$ values in the TLC systems indicated below:

| Elution system (v/v) | $R_f$ value |
|---|---|
| (I) Acetonitrile/water 75:25 | 0.53 |
| (silica gel Merck 60 F$_{254}$) | |
| (II) Acetonitrile/5% aqueous sodium sulfate 30:70 | 0.54 |
| (silica gel Merck silanized 60 F$_{254}$) | |
| Visualization: UV-light at 254 nm; 3% ethanolic ninhydrine; 1% methanolic fluorescamine; | |

(g) a retention time ($t_R$) of 10.8 minutes when analyzed by reversed phase HPLC using a 150×4.0 mm Zorbax® ODS (5–6 μm) column (Zorbax is a trademark of the Dupont Co. for a octadecylsilane silica matrix), and eluting with a linear gradient from 0% to 50% solution B in solution A in 40 minutes solution A: 25 mM NaH$_2$PO$_4$/acetonitrile (9/1) buffered at pH 6.0 with 0.1 N NaOH solution B: 25 mM NaH$_2$PO$_4$/acetonitrile (3/7) buffered at pH 6.0 with 0.1 N NaOH), with a flow rate of 2 ml/min.; (internal standard: 3,5-dihydroxytoluene $t_R$ 5.60 minutes)

(h) the $^1$H NMR spectrum registered at 270 MHz in DMSO-d$_6$ at 60° C. and with a sample concentration of 20 mg/ml is reported in FIG. 3 (internal standard, TMS δ=0.00 ppm).

Some of the $^1$H NMR data obtained after D$_2$O exchange and selective decoupling experiments are as follows (δ ppm, multiplicity): 1.86, s; 2.81, d; 3.5, dd; ~3–4; 4.12, d; 4.32, d; 4.37, d; 4.56, s; 4.95, ddd; 5.07, s; 5.31, d; 5.39, s; 5.51, s; 5.66, d; 6.12, d; 6.29, s; 6.32, s; 6.37, s; 6.42, s; 6.60, d; 6.62, s; 6.64, d; 6.92, d; 7.09, s; 7.12, d; 7.21, d; 7.25, d; 7.43, d; 7.64, d; 7.66, d; 7.70, d; 7.85, s; 8.12, d; 8.46, d; ~9.5, s.

(i) a potentiometric titration profile which shows three titration slopes with pH½ values equal to 5.0 (one equivalent), 7.0 (one equivalent), and 11 (five equivalents) in methylcellosolve:water 4:1 upon titration with 0.01 N NaOH of the solution of the test compound containing an excess of 0.01 N HCl in same solvent mixture (l) an acidic function capable of forming salts (m) a basic function capable of forming salt (n) a sugar residue which is N-acetyl-D-glucosamine.

On the basis of the physico-chemical data and by comparison with other glycopeptidic antibiotic substances, such as vancomycin and ristocetin, the following structure can tentatively be attributed to antibiotic L 17046:

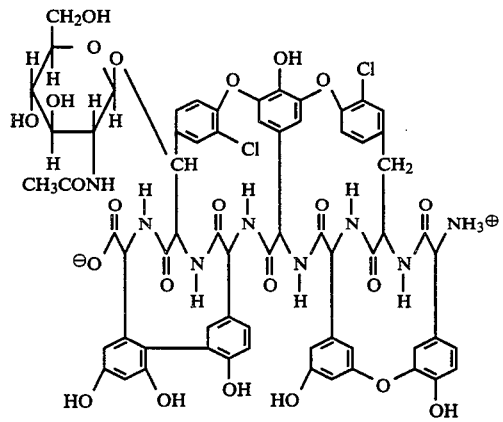

Physico-Chemical Characteristics of Antibiotic L 17054

Antibiotic L 17054 has the following characteristics:

(a) the specific rotation $[\alpha]_D^{20}$ is $-34°$ (c=1%, DMF)

(b) it is freely soluble in water at pH>8.0, in dimethylformamide, dimethylsulfoxide, propyleneglycol and methylcellosolve; slightly soluble in methanol; almost insoluble in ethyl ether and acetone.

(c) an ultraviolet absorption spectrum which has the following absorption maxima:

in 0.1 N hydrochloric acid: $\lambda_{max}$278 nm (E$_1$ cm$^1$%=60.6)

in 0.1 N sodium hydroxide: $\lambda_{max}$297 nm (E$_1$ cm$^1$%=118.8)

in phosphate buffer pH 7.4: $\lambda_{max}$277 nm (E$_1$ cm$^1$%=70.3)

(d) an infrared absorption spectrum in nujol with the following absorption maxima (cm$^{-1}$): 3700–2000, 2970–2850 (nujol), 1655, 1610, 1595, 1515, 1490, 1460 (nujol), 1375 (nujol), 1300, 1230, 1145, 1060, 1020, 970, 890, 850, 820, 720 (nujol)

(e) an elemental analysis, after the sample has been previously dried at about 140° C. under inert atmosphere (weight loss=7.8%), which indicated the following approximate percentage composition (average): carbon 55.46%; hydrogen, 4.50%; nitrogen 7.20%; chlorine 4.67%; ashes 0.2%

(f) it has the following $R_f$ values in the TLC systems indicated below:

| Elution system (v/v) | $R_f$ value |
|---|---|
| (I) Acetonitrile/water 75:25 | 0.32 |
| (silica gel Merck 60 F$_{254}$) | |
| (II) Acetonitrile/5% aqueous sodium sulfate 30:70 | 0.61 |
| (silica gel Merck silanized 60 F$_{254}$) | |
| Visualization: UV-light at 254 nm; 3% ethanolic ninhydrine; 1% methanolic fluorescamine; | |

(g) a retention time ($t_R$) of 8.3 minutes when analyzed by HPLC using a 150×4.0 mm Zorbax® ODS (5–6 μm) column (Zorbax is a trademark of the Dupont Co. for an octadecylsilane silica gel matrix), and eluting with a linear gradient from 0% to 50% solution B in solution A in 40 minutes (solution A: 25 mM NaH$_2$PO$_4$/acetonitrile (9/1) buffered at pH 6.0 with 0.1 N NaOH; solution B: 25 mM NaH$_2$PO$_4$/acetonitrile (3/7) buffered at pH 6.0 with 0.1 N NaOH), with a flow rate of 2 ml/min.; (internal standard: 3,5-dihydroxytoluene $t_R$ 5.60 minutes)

(h) the $^1$H NMR spectrum is registered at 270 MHz in DMSO-$d_6$ at 60° C. and with a sample concentration of 20 mg/ml (internal standard, TMS $\delta = 0.00$ ppm). Some of the $^1$H NMR data obtained after $D_2O$ exchange and selective decoupling experiments are as follows ($\delta$ ppm, multiplicity): 1.88, s; 2.85, d; ~3.5, dd; 3–4; 4.20, d; 4.48, d; 4.50, d; 4.62, s; 4.96, ddd; 5.18 d; 5.31, s; 5.35, d; 5.39, s; 5.68, d; 5.71, s; 6.20, d; 6.41, s; 6.51, s; 6.56, s; 6.74, d; 6.77, s; 6.80, s; 6.80, d; 6.98, d; 7.08, s; 7.15, d; 7.21, d; 7.28, d; 7.35, d; 7.50, d; 7.56, d; 7.64, d; 7.73, d; 7.86, s; 8.42, d.

(i) a potentiometric titration profile which shows three titration slopes with pH½ values equal to 5.0 (one equivalent), 7.0 (one equivalent), and 11 (five equivalents) in methylcellosolve:water 4:1 upon titration with 0.01 N NaOH of the solution of the test compound containing an excess of 0.01 N HCl in the same solvent mixture (l) an acidic function capable of forming salts (m) a basic function capable of forming salts (n) two sugar residues which are D-mannose and N-acetyl-D-glucosamine.

Antibiotic L 17046 possesses acid and basic functions capable of forming salts respectively with bases and acids and therefore it can be transformed into its pharmaceutically acceptable acid and/or basic addition salts according to procedures known per se in the art. The acid addition salts are prepared as known in the art, preferably by using mineral acids or rather strong acids in general such as hydrohalic, sulfuric, phosphoric, nitric, acetic, citric, aspartic, methanesulfonic, toluenesulfonic, or sulfanilic acid.

The basic addition salts, such as the alkali metal, the alkaline earth metal, the ammonium and organic ammonium salts such as the alkylammonium salts are prepared as known in the art. In some instances they can be preferred in view of their easy preparation and desirable solubility properties. The basic addition salts also encompass basic aminoacid addition salts such as the lysine, arginine or glycine salts.

In view of the similarity of the properties of antibiotic L 17046 and its salts, what is said in the present application when dealing with the biological activities of antibiotic L 17046 applies also to its pharmaceutically acceptable salts.

The in vitro antibacterial activity of antibiotic L 17046, which showed to be mainly active against gram-positive bacteria, was determined by using the two-fold dilution method in microtiter system. Isosensitest broth (Oxoid) and Todd-Hewitt broth (Difco) were used for Staphylococci and Streptococci, respectively. Broth cultures were diluted so that the final inoculum was about $10^4$ colony forming units/ml (CFU/ml). Minimal inhibitory concentration (MIC) was considered as the lowest concentration which showed no visible growth after 18–24 h incubation at 37° C. The obtained results are summarized in TABLE I below:

TABLE I

| In vitro antibacterial activity of antibiotic L 17046 | |
|---|---|
| Microorganism | MIC (μg/ml) |
| Staphylococcus aureus ATCC 6538 | 0.2 |
| Staplylococcus aureus Tour | 0.2 |
| Staplylococcus aureus Tour (Isosensitest broth + 30% bovine serum) | 0.4 |
| Staphylococcus epidermidis ATCC 12228 | 0.05 |
| Streptococcus pyogenes C 203 | 1.6 |

TABLE I-continued

| In vitro antibacterial activity of antibiotic L 17046 | |
|---|---|
| Microorganism | MIC (μg/ml) |
| Streptococcus dysgalactiae ATCC 9926 | 0.8 |
| Streptococcus faecalis ATCC 7080 | 1.6 |
| Streptococcus pneumoniae UC 41 | 1.6 |

Antibiotic L 17046 was found to be particularly effective against coagulase-negative staphylocci (S. epidermidis, S. saprophyticus).

Its MICs (g/ml) against some clinical isolates of the above microbial strains are listed below in Table II:

TABLE II

| Strains | MIC (μg/ml) |
|---|---|
| S. epidermidis *L 785 | 0.05 |
| S. epidermidis L 1378 | 0.05 |
| S. epidermidis *L 835 | 0.1 |
| S. epidermidis *L 1142 | 0.1 |
| S. saprophyticus L 1141 | 0.1 |

*Methicillin-resistant strains

The antimicrobial activity of the compound of the invention is confirmed also in in vivo experiments.

The approximate acute toxicity in mice (i.p.) of antibiotic L 17046 was evaluated according to methods known in the art and the approximate $LD_{50}$ was found to be about 850 mg/kg in mice administered by i.m. route.

In view of the above, the compound of the present invention can effectively be employed as the active ingredient of antimicrobial preparations used in human and veterinary medicine for the prevention and treatment of infectious diseases caused by pathogenic bacteria which are susceptible to said active ingredients. The compounds of the present invention can be administered orally, topically or parenterally. However, the parenteral and topical routes of administration are preferred. Particularly preferred are those pharmaceutical formulations suitable for intramuscular administration. Depending on the route of admnistration, these compounds can be formulated into various dosage forms. The formulation of suitable pharmaceutical compositions can be carried out by the skilled man according to the general common knowledge in the art with the auxilium of reference books, such as the "Remington's Pharmaceutical Sciences" Handbook, Mack Publishing Company, U.S.A., 15th Edition, 1975.

For topical use the compounds of the present invention may be prepared in suitable forms for absorption through the mucous membranes of the nose and throat or bronchial tissues and may conveniently take the form of liquid sprays or inhalants, lozenges, or throat paints. For medication of the eyes or ears, the preparation may be presented in liquid or semi-liquid form. Topical applications may be formulated in hydrophobic or hydrophilic bases as ointments, creams, lotions, paints, or powders.

Compositions for injection may take such forms as suspensions, solutions, or emulsions in oily or aqueous vehicles, and may contain formulatory agents such as preservative, suspending, stabilizing and/or dispersing agents.

Alternatively, the active ingredient may be in powder form for reconstitution, at the time of delivery, with a suitable vehicle, such as sterile water.

The active compound may also be formulated into suppositories for rectal, vaginal or urethral administration. The excipient are those usually used in these preparations such as polyvinylpyrrolidone, cocoa butter, triglycerides of $C_{12}$–$C_{18}$ fatty acids, polyethylene glycols and surface-active agents.

The amount of compound administered will vary with the severity of the infection, the nature and body weight of the patient, the type and formulation in which the active ingredient is to be administered, the mode of administration, the general health status of the patient, and the interval between each subsequent administration.

In consideration of the above parameters, sometimes it may be necessary to deviate from the dosage-range indicated. In general, antibiotic L 17046 and its pharmaceutically acceptable salts are effective at a daily dosage comprised between about 0.1 and about 20 mg of active ingredient per Kg of body weight, preferably divided in 2 to 4 administrations per day.

Particularly desirable compositions are those prepared in the form of dosage units containing from about 5 to about 250 mg of the active principle per unit.

Representative examples of preparation of pharmaceutical compositions are as follows:

A parenteral solution is prepared with 100 mg of antibiotic L 17046 sodium salt dissolved in 2 ml of sterile water for injection A parenteral solution is prepared with 250 mg of antibiotic L 17046 sodium salt dissolved in 3 ml of sterile water for injection A topical ointment is prepared with 200 mg of antibiotic L 17046; 600 mg of polyethylene glycol 4000 U.S.P; 1.2 g of polyethylene glycol 400 U.S.P.

Besides their activity as medicaments, the compound of the present invention can be used as animal growth promoters.

For this purpose, the compound of the invention are administered orally in a suitable feed. The exact concentration employed is that which is required to provide for the active agent in a growth promotant effective amount when normal amounts of feed are consumed.

The addition of the active compounds of the invention to animal feed is preferably accomplished by preparing an appropriate feed premix containing the active compounds in an effective amount and incorporating the premix into the complete ration.

Alternatively, an intermediate concentrate or feed supplement containing the active ingredient can be blended into the feed.

The way in which such feed premixes and complete rations can be prepared and administered are described in reference books (such as "Applied Animal Nutrition", W. H. Freedman and Co., S. Francisco, USA, 1969 or "Livestock Feeds and Feeding", O and B Books, Corvallis, Oreg., USA, 1977) and are incorporated herein by reference.

The following examples illustrate the manner in which the invention can be practiced, but, as such, should not be construed as limiting its overall scope.

Example 1: Preparation of antibiotic L 17046 from teicoplanin

Teicoplanin $A_2$ (10 g) is added to 1 N hydrochloric acid (150 ml) preheated to 80° C. while stirring. After about 45 minutes the reaction mixture is cooled to 0°–5° C. and 37% hydrochloric acid (30 ml) is added. Stirring is maintained for about 10 minutes, after which the precipitated solid is recovered by filtration, washed with 20 ml of 2 N HCl, then with ethyl ether, and dried overnight over potassium hydroxide pellets at room temperature, resulting in the crude product of the title (8.3 g).

Example 2: Purification of crude antibiotic L 17046

The above crude product (6.2 g) is dissolved in 80% methanol (500 ml) and silica gel (30 g; Merck 0.06–0.2 mm) is added. After the addition of n.butanol (200 ml) the solvent is removed under vacuum. The residue is then applied to a silica gel chromatography column (300 g) in acetonitrile.

The column is developed by using sequentially 300 ml each of the following solvent mixtures:

acetonitrile, acetonitrile:water 95:5, acetonitrile:water, 90:10; acetonitrile:water, 85:15.

The eluates are discarded and the column is developed with a linear gradient eluent obtained by mixing 3.5 l each of the following mixtures:

acetonitrile:water, 83:17 and acetonitrile:water, 70:30 at a rate of 375 ml/h.

Fractions of 25 ml each are collected and monitored by HPLC. The fractions which contain antibiotic L 17046 (fractions 170 to 200) are combined. n-Butanol (400 ml) is added to the pooled fractions and the resulting mixture is concentrated to a small volume. Acetone is then added to the cloudy solution and, after cooling to 10° C. a precipitate begins to form. After suitable time, the precipitation is complete and the solid is then collected by filtration, washed with acetone, then with ether, dried under vacuum at room temperature, yielding the pure compound of the title (1.9 g).

Example 3: Preparation of antibiotic L 17046 from antibiotic L 17054

(a) Preparation of antibiotic L 17054

5 g of teicoplanin are added to 60 ml of 0.5 N aqueous hydrochloric acid pre-heated to 80° C. with vigorous stirring.

Stirring is continued and the temperature is maintained at about 80° C. for 30 minutes. Then, the mixture is rapidly filtered, the filtrate is cooled to 0°–5° C. and 6 N hydrochloric acid (10 ml) is added. The resulting suspension is stirred for about 15 minutes while keeping the temperature at 0°–5° C. The precipitate is collected, washed and dried under reduced pressure at room temperature resulting in crude antibiotic L 17054 (4.5 g).

Crude antibiotic L 17054 (3 g) as obtained in Example 1 is suspended in a mixture of 0.2% aqueous $HCOONH_4$:$CH_3CN$ 95:5 (v/v) (150 ml).

The pH is brought to pH 7.5 with 1 N NaOH and the product is dissolved. The resulting solution is applied to a column containing 150 g of 0.06–0.2 mm silanized silica gel (Merck) prepared in the same solvent mixture. The column is developed with a linear gradient elution, from 5 to 21% of acetonitrile in 0.2% aqueous ammonium formate (v/v), collecting 20 ml fractions, which are monitored by HPLC. L 17054 containing fractions (70 to 96) are combined and the acetonitrile is removed under vacuum. The residual aqueous solution is applied to a column of 10 g of silanized silica gel in distilled water. After washing with distilled water until the salts are completely eliminated the product is eluted with a 1:1 (v/v) $CH_3CN$:$H_2O$ mixture.

The collected solution is concentrated under vacuum to a small volume, acidified to pH 3.5 with 1 N HCl and the antibiotic is precipitated by adding acetone. After drying at room temperature, 0.9 g of pure antibiotic L 17054 is obtained.

(b) Production of antibiotic L 17046:

1 N Hydrochloric acid (15 ml) is heated to 80° C. and the antibiotic L 17054 (1 g) is added, while keeping the temperature at 80° C. The stirred mixture is kept at this temperature for about 30 minutes, then it is cooled to 0°-5° C. and 37% hydrochloric acid (1 ml) is added. Stirring is maintained for about 10 minutes, then the solid is recovered by filtering, washing and drying under reduced pressure, at room temperature, overnight resulting in the crude antibiotic L 17046 (0.5 g) which can be purified essentially as described above in Example 2.

We claim:

1. A compound selected from antibiotic L 17046 and its pharmaceutically acceptable salts which has the following characteristics, in the non-salt form:
   (a) the specific rotation $[\alpha]_D^{20}$ is $-44°$ (c=1%, DMF)
   (b) it is freely soluble in water at pH>8.0, in dimethylformamide, dimethylsulfoxide, propyleneglycol and methylcellosolve; slightly soluble in methanol; almost insoluble in n-hexane, ethyl ether and acetone,
   (c) it has an ultraviolet absorption spectrum that exhibits the following absorption maxima:
      in 0.1 N hydrochloric acid: $\lambda_{max}278$ nm ($E_1^{cm1\%}=67.1$)
      in 0.1 N sodium hydroxide: $\lambda_{max}297$ nm ($E_1^{cm1\%}=124.1$)
      in phosphate buffer pH 7.4: $\lambda_{max}277$ nm ($E_1^{cm1\%}=75.0$)
   (d) an infrared absorption spectrum in nujol with the following observable absorption maxima ($cm^{-1}$): 3700-2000, 2970-2850 (nujol), 1655, 1610, 1595, 1515, 1490, 1460 (nujol), 1375 (nujol), 1300, 1230, 1145, 1060, 1010, 890, 850, 820, 720 (nujol)
   (e) an elemental analysis, after the sample has been previously dried at about 140° C. under inert atmosphere (weight loss=8.4%), which indicates the following approximate percentage composition (average): carbon 56.74%; hydrogen, 4.27%; nitrogen, 7.99%; chlorine, 5.11%; ashes, 0.6%
   (f) the following $R_f$ values in the TLC systems indicated below:

| Elution system (v/v) | $R_f$ value |
|---|---|
| (I) Acetonitrile/water 75:25 (silica gel Merck 60 F$_{254}$) | 0.53 |
| (II) Acetonitrile/5% aqueous sodium sulfate 30:70 (silica gel Merck silanized 60 F$_{254}$) | 0.54 |
| Visualization: UV light at 254 nm; 3% ethanolic ninhydrine; 1% methanolic fluorescamine; | |

(g) a retention time ($t_R$) of 10.8 minutes when analyzed by reversed phase HPLC using a 150×4.0 mm Zorbax ® ODS (5-6 μm) column (Zorbax is a trademark of the Dupont Co. for a octadecylsilane silica matrix) and eluting with a linear gradient from 0% to 50% solution B in solution A in 40 minutes
      solution A: 25 mM NaH$_2$PO$_4$/acetonitrile (9/1) buffered at pH 6.0 with 0.1 N NaOH
      solution B: 25 mM NaH$_2$PO$_4$/acetonitrile (3/7) buffered at pH 6.0 with 0.1 N NaOH), with a flow rate of 2 ml/min.;
      (internal standard: 3,5-dihydroxytoluene $t_R$ 5.60 minutes)
   (h) the $^1$H NMR spectrum registered at 270 MHz in DMSO-d$_6$ at 60° C. and with a sample concentration of 20 mg/ml is reported in FIG. 3 (internal standard, TMS $\delta=0.00$ ppm),
   some of the $^1$H NMR data obtained after D$_2$O exchange and selective decoupling experiments are as follows (δ ppm, multiplicity): 1.86, s; 2.81, d; 3.5, dd; ~3–4; 4.12, d; 4.32, d; 4.37, d; 4.56, s; 4.95, ddd; 5.07, s; 5.31, d; 5.39, s; 5.51, s; 5.66, d; 6.12, d; 6.29, s; 6.32, d; 6.37, s; 6.42, s; 6.60, d; 6.62, s; 6.64, d; 6.92, d; 7.09, s; 7.12, d; 7.21, d; 7.25, d; 7.43, d; 7.64, d; 7.66, d; 7.70, d; 7.85, s; 8.12, d; 8.46, d; ~9.5, s,
   (i) a potentiometric titration profile which shows three titration slopes with pH½ values equal to 5.0 (one equivalent), 7.0 (one equivalent), and 11 (five equivalents) in methylcellosolve:water 4:1 upon titration with 0.01 N NaOH of the solution of the test compound containing an excess of 0.01 N HCl in the same solvent mixture
   (1) an acidic function capable of forming salts,
   (m) a basic function capable of forming salts,
   (n) a sugar residue which is N-acetyl-D-glucosamine.

2. Antibiotic L 17046 or a pharmaceutically acceptable salt thereof, characterized by the following formula, in the non-salt form:

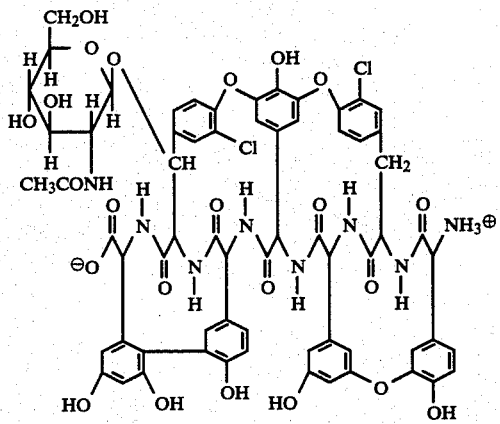

* * * * *